United States Patent
Hao et al.

(10) Patent No.: US 9,877,982 B2
(45) Date of Patent: Jan. 30, 2018

(54) IMMUNOASSAY OF S-ADENOSYLMETHIONINE USING ANALOGS THEREOF AND PERSONALIZED THERAPEUTICS

(71) Applicants: Xiujuan Hao, Chantilly, VA (US); Isaac A Angres, Arlington, VA (US)

(72) Inventors: Xiujuan Hao, Chantilly, VA (US); Isaac A Angres, Arlington, VA (US)

(73) Assignee: Hunan SkyWorld Biotechnologies Co. LTD, Changsha (CN)

( * ) Notice: Subject to any disclaimer, the term of this patent is extended or adjusted under 35 U.S.C. 154(b) by 61 days.

(21) Appl. No.: 14/218,928

(22) Filed: Mar. 18, 2014

(65) Prior Publication Data

US 2014/0271945 A1    Sep. 18, 2014

Related U.S. Application Data

(60) Provisional application No. 61/801,547, filed on Mar. 15, 2013.

(51) Int. Cl.
*G01N 33/574* (2006.01)
*A61K 31/7076* (2006.01)

(52) U.S. Cl.
CPC ... *A61K 31/7076* (2013.01); *G01N 33/57484* (2013.01); *G01N 2800/7033* (2013.01)

(58) Field of Classification Search
CPC ......... A61K 31/7076; G01N 33/57484; G01N 2800/7033
See application file for complete search history.

(56) References Cited

U.S. PATENT DOCUMENTS

| | | | |
|---|---|---|---|
| 8,344,115 B2* | 1/2013 | Chang | C07K 16/44 436/544 |
| 8,728,732 B2* | 5/2014 | Guerrero-Preston | C12Q 1/6886 435/6.11 |
| 2009/0263879 A1* | 10/2009 | Chang | C07K 16/44 435/183 |

OTHER PUBLICATIONS

Yu et al. Progressive disease in chronic lymphocytic leukemia is correlated with the DNA methylation index. Leukemia Research 2007, vol. 31, pp. 773-777.*

* cited by examiner

*Primary Examiner* — Shafiqul Haq
(74) *Attorney, Agent, or Firm* — Isaac Angres

(57) ABSTRACT

A method of detecting the presence or absence of a disease in a patient wherein said disease is accompanied by deficient levels of S-adenosylmethionine comprising: identifying a patient that is suspected of having said disease or is at risk of having said disease; obtaining a biological sample from said patient; determining the level of S-adenosylmethionine in said biological sample using an antibody derived from a hapten analog of S-adenosylmethionine; and correlating the level of S-adenosylmethionine in said biological sample with the presence or absence of said disease. The invention also provides methods for measuring SAH which is used to determine the methylation index (ratio of SAM/SAH) in biological fluids which is indicative of the health status of an individual.

1 Claim, 6 Drawing Sheets

IMMUNOASSAY OF S-ADENOSYLMETHIONINE USING ANALOGS THEREOF AND PERSONALIZED THERAPEUTICS

This application claims the priority benefit under 35 U.S.C. section 119 of U.S. Provisional Patent Application No. 61/801,547 entitled "Immunoassay Of S-Adenosylmethionine In Personalized Medicine And Health Or Cancer Evaluation" filed on Mar. 15, 2013, and which is in its entirety herein incorporated by reference.

FIELD OF THE INVENTION

The present invention generally relates to measuring levels of S-adenosylmethionine in biological fluids as a marker of many diseases.

The instant invention also relates to measuring levels of S-adenosylmethionine in biological fluids as a marker of many diseases by using antibodies raised against analogs thereof.

The present invention relates to measuring levels of S-adenosylmethionine in biological fluids as a marker of disease and correlating the levels to disease progression and determining the proper therapeutic protocol based on the levels of S-adenosylmethionine.

This invention also relates to diagnostic, screening, and early detection methods for cancer, which can also be used to monitor therapeutic effectiveness and relapse monitoring in cancer and other pathological and physiological processes.

The present invention is also directed to a system for developing target specific assays for determining whether a patient will likely respond to a target specific drug, and more particularly to a such a system that is highly economical and provides synergies when diagnostics and drugs are developed in parallel.

The instant invention is also directed to a method for discovering, screening, searching, identifying, developing and/or evaluating the measurement of the methylation index for correlating disease progression and disease treatments and response to said treatments.

The present invention also relates to using the methylation index (or methylation status in some of the literature. In this filing we use methylation index to represent SAM/SAH) as a biomarker, methods, devices, reagent, systems and kits for the detection, diagnosis of cancer as well as other diseases and for the monitoring of cancer progression and for monitoring the progress of various cancer treatments and other diseases. Cancer progression is characterized by progressively increased levels of global DNA hypomethylation, regional CpG hypermethylation, and genomic instability. Decreased methylation index is co-related with the global DNA hypomethylation and genomic instability. Therefore, it is a good marker to help evaluate health status and disease progression or stages.

BACKGROUND OF THE INVENTION

S-Adenosylmethionine (SAMe) is found in almost every tissue and fluid in the body. SAM plays a crucial role in the process called transmethylation. Methylation is involved in nearly every aspect of life. SAM is the primary "methyl" donor for a variety of methyl-transfer reactions in DNA, RNA, proteins, lipids, and small molecules in the body. Proper DNA methylation is essential for normal embryonic development. Methyl-transferase gene homozygously deleted (knocked out) has been proven lethal (Pegg, A. E., Feith, D. J., Fong, L. Y., Coleman, C. S., O'Brian, T. G., and Shantz, L. M., 2003, Biochem. Soc. Trans. 31, 356-360). DNA improperly methylated has been found in many tumors. Alterations in DNA methylation patterns induce the expression of oncogens or silence the expression of tumor suppressor genes, and methyl deficient diets have been shown to promote liver cancer in rodents.

The transsulfuration begins with S-adenosylhomocysteine (SAH), the residual structure of SAM upon donating the methyl group (transmethylation). Hydrolysis of SAH yields homocysteine, which in turns converts to cystathionine, then cysteine, and eventually, to glutathione, the hepatocellular antioxidant and life-saving detoxification agent.

The aminopropylation is another process initiated with SAM through decarboxylation. The decarboxylated SAM then couples with putrescine to generate spermidine and spermine which are critical to cell growth, differentiation and the stability of DNA and RNA. Furthermore, Methylthioadenosine (MTA), the by-product of polyamine synthesis, is a powerful analgesic and anti-inflammatory agent. This may be, at least partially, responsible for the clinical benefits observed in the treatment of osteoarthritis, rheumatoid arthritis and fibromyalgia with SAMe.

SAMe plays a role in the immune system, maintains cell membranes, and helps produce and break down brain chemicals, such as serotonin, melatonin, and dopamine. Deficiency of either vitamin B12 or foliate can reduce the level of SAMe. SAMe is also an antioxidant, a substance that protects the body from damaging reactive oxygen molecules in the body. These reactive oxygen molecules can come from inside the body or from environmental pollution and are thought to play a role in the aging process and the development of degenerative disease. In general, SAMe is thought to raise the level of functioning of other amino acids in the body.

By way of further background, S-adenosyl-1-methionine is a substrate of an enzyme lyase that converts S-adenosyl-1-methionine to the molecule methylthioadenosine and homoserine; it is an aminobutyric chain donor to tRNA; it is an aminoacidic chain donor in the biosynthesis of biotin; SAM-e, after decarboxylation, is the donor of aminopropyl groups for the biosynthesis of neuroregulatory polyamines spermidine and spermine. (Zappia et al (1979), Biomedical and Pharmacologcial roles of Adenosylmethionine and the Central Nervous System, page 1, Pergamon Press. N.Y.)

SAM-e has been used clinically in the treatment of liver disease (Friedel H, Goa, K. L., and Benfield P., (1989), S-Adenosyl-1-methionine: a review of its pharmacological properties and therapeutic potential in liver dysfunction and affective disorders in relation to its physiological role in cell metabolism. Drugs. 38, 389-416), arthritis (Di Padova C, (1987), S-adenosyl-1-methionine in the treatment of osteoarthritis: review of the clinical studies. Am J. Med. 83, (Suppl. 5), 6-65), and depression (Kagan, B, Sultzer D. L., Rosenlicht N and Gerner R. (1990), Oral S-adenosylmethionine in depression: a randomized, double blind, placebo-controlled trial. Am. J. Psychiatry 147, 591-595.) Alzheimer's patients have reduced cerebral spinal fluid levels of S-adenosyl-1-methionine (Bottiglieri et al, (1990), Cerebrospinal fluid S-adenosyl-1-methionine in depression and dementia: effects of treatment with parenteral and oral S-adenosyl-1-methionine. J. Neurol. Neurosurg. Psychiatry 53, 1096-1098.) In a preliminary study, SAM-e was able to produce cognitive improvement in patients with Alzheimer's disease. (Bottiglieri et al (1994), The clinical potential of admetionine (S-adenosyl-1-methioinine) in neurological disorders. Drugs 48, 137-152.) SAM-e brain levels in patients with Alzheimer's disease are also severely decreased. (Morrison et al, (1996), Brain S-adenosylmethionine levels are severely decreased in Alzheimer's disease, Journal of Neurochemistry, 67, 1328-1331.) Patients with Parkinson's disease have also been shown to have significantly decreased blood levels of SAM-e. (Cheng et al, (1997), Levels of L-methionine S-adenosyltransferase activity in erythrocytes and concentrations of S-adenosylmethionine and S-adenosylhomocysteine in whole blood of patients with Parkinson's disease. Experimental Neurology 145, 580-585.)

SAM-e levels in patients treated with the antineoplastic drug methotrexate are reduced. Neurotoxicity associated with this drug may be attenuated by co-administration of SAM-e. (Bottiglieri et al (1994), The Clinical Potential of Ademetionine (S-adenosylmethionine) in neurological disorders, Drugs, 48 (2), 137-152.)

Cerebral spinal fluid levels of SAM-e have been investigated in HIV AIDS dementia Complex/HIV encephalopathy and found to be significantly lower than in non-HIV infected patients. (Keating et al (1991), Evidence of brain methyltransferase inhibition and early brain involvement in HIV positive patients Lancet: 337:935-9.)

De La Cruz et al have shown that SAM-e, chronically administered, can modify the oxidative status in the brain by enhancing anti-oxidative defenses. (De La Cruz et al, (2000), Effects of chronic administration of S-adenosyl-1-methionine on brain oxidative stress in rats. Naunyn-Schmiedeberg's Archives Pharmacol 361: 47-52.) This is similar to results obtained with SAM-e in liver and kidney tissue. Thus SAM-e would be useful as an antioxidant.

Oral SAM-e administration to patients with and without liver disease has resulted in increases in liver glutathione levels. (Vendemiale G et al, (1989), Effect of oral S-adenosyl-1-methionine on hepatic glutathione in patients with liver disease. Scand J Gastroenterol; 24: 407-15. Oral administration of SAM-e to patients suffering from intrahepatic cholestasis had improvements in both the pruritus as well as the biochemical markers of cholestasis. (Giudici et al, The use of admethionine (SAM-e) in the treatment of cholestatic liver disorders. Meta-analysis of clinical trials. In: Mato et al editors. Methionine Metabolism: Molecular Mechanism and Clinical Implications. Madrid: CSIC Press; 1992 pp 67-79.) Oral SAM-e administration to patients suffering from primary fibromyalgia resulted in significant improvement after a short term trial. (Tavoni et al, Evaluation of S-adenosylmethioine in Primary Fibromaylgia. The American Journal of Medicine, Vol 83 (suppl 5A), pp 107-110, 1987.) SAM-e has been used for the treatment of osteoarthritis as well. (Koenig B. A long-term (two years) clinical trial with S-adenosylmethionine for the treatment of osteoarthritis. The American Journal of Medicine, Vol 83 (suppl 5A), Nov. 20, 1987 pp 89-94)

SAM-e is clinically useful in many apparently unrelated areas because of its important function in basic metabolic processes. One of its most striking clinical uses is in the treatment of alcoholic liver cirrhosis that, until now, remained medically untreatable. Mato et al demonstrated the ability of oral SAM-e in alcoholic liver cirrhosis to decrease the overall mortality and/or progression to liver transplant by 29% vs 12% as compared with a placebo treated group. (Mato et al (1999), S-adenosylmethionine in alcohol liver cirrhosis: a randomized, placebo-controlled, double blind, multi-center clinical trial, Journal of Hepatology, 30, 1081-1089.)

Sam-e also attenuates the damage caused by tumor necrosis factor alpha and can also decrease the amount of tumor necrosis factor alpha secreted by cells. Consequently, conditions in which this particular inflammatory factor is elevated would benefit from the administration of SAM-e. (Watson W H, Zhao Y, Chawla R K, (1999) Biochem J August 15; 342 (Pt 1):21-5. S-adenosylmethionine attenuates the lipopolysaccharide-induced expression of the gene for tumour necrosis factor alpha.) SAM-e has also been studied for its ability to reduce the toxicity associated with administration of cyclosporine A, a powerful immunosuppressor. (Galan A, et al, Cyclosporine A toxicity and effect of the s-adenosylmethionine, Ars Pharmaceutica, 40:3; 151-163, 1999.)

SAM-e, incubated in vitro with human erythrocytes, penetrates the cell membrane and increases ATP within the cell thus restoring the cell shape. (Friedel et al, S-adenosyl-1-methionine: A review of its pharmacological properties and therapeutic potential in liver dysfunction and affective disorders in relation to its physiological role in cell metabolism, Drugs 38 (3):389-416, 1989)

SAM-e has been studied in patients suffering from migraines and found to be of benefit. (Friedel et al, S-adenosyl-1-methionine: A review of its pharmacological properties and therapeutic potential in liver dysfunction and affective disorders in relation to its physiological role in cell metabolism, Drugs 38 (3): 389-416, 1989)

SAM-e has been administered to patients with peripheral occlusive arterial disease and was shown to reduce blood viscosity, chiefly via its effect on erythrocyte deformability.

SAM-e is commercially available using fermentation technologies that result in SAM-e formulations varying between 60 and 80% purity. (That is, the final product contains 60-80% of the active or (S, S)-SAM-e and 20-40% of the inactive or (R, S)-SAM-e.) (Gross, A., Geresh, S., and Whitesides, Gm (1983) Appl. Biochem. Biotech. 8, 415.) Enzymatic synthetic methodologies have been reported to yield the inactive isomer in concentrations exceeding 60%. (Matos, J R, Rauschel F M, Wong, C H. S-Adenosylmethionine: Studies on Chemical and Enzymatic Synthesis. Biotechnology and Applied Biochemistry 9, 39-52 (1987). Enantiomeric separation technologies have been reported to resolve the pure active enantiomer of SAM-e. (Matos, J R, Rauschel F M, Wong, C H. S-Adenosylmethionine: Studies on Chemical and Enzymatic Synthesis. Biotechnology and Applied Biochemistry 9, 39-52 (1987; Hoffman, Chromatographic Analysis of the Chiral and Covalent Instability of S-adenosyl-1-methionine, Biochemistry 1986, 25 4444-4449: Segal D and Eichler D, The Specificity of Interaction between S-adenosyl-1-methionine and a nucleolar 2-O-methyltransferase, Archives of Biochemistry and Biophysics, Vol. 275, No. 2, December, pp. 334-343, 1989) Newer separation technologies exist to resolve enantiomers on a large commercial production scale at a very economic cost. In addition, it would be conceivable to synthesize the biologically active enantiomer using special sterioselective methodologies but this has not been accomplished to date.

De la Haba first showed that the sulfur is chiral and that only one of the two possible configurations was synthesized and used biologically. (De la Haba et al J. Am. Chem. Soc. 81, 3975-3980, 1959) Methylation of RNA and DNA is essential for normal cellular growth. This methylation is carried out using SAM-e as the sole or major methyl donor with the reaction being carried out by a methyltransferase enzyme. Segal and Eichler showed that the enzyme bound (S, S)-SAM-e 10 fold more tightly than the biologically inactive (R, S)-SAM-e thus demonstrating a novel binding stereospecificity at the sulfur chiral center. Other methyltransferases have been reported to bind (R, S)-SAM-e to the same extent as (S, S)-SAM-e and thus (R, S)-SAM-e could act as a competitive inhibitor of that enzyme. (Segal D and Eichler D, The Specificity of Interaction between S-adenosyl-1-methionine and a nucleolar 2-O-methyltransferase, Archives of Biochemistry and Biophysics, Vol. 275, No. 2, December pp. 334-343, 1989; Borchardt R T and Wu Y S, Potential inhibitors of S-adenosylmethionine-dependent methyltransferases. Role of the Asymmetric Sulfonium Pole in the Enzymatic binding of S-adenosyl-1-methionine, Journal of Medicinal Chemistry, 1976, Vol 19, No. 9, 1099-1103.)

SAM-e (whether in its optically pure enantiomeric form or in an enantiomeric or racemic mixture) presents certain difficult problems in terms of its stability at ambient temperature that result in degradation of the molecule to undesirable degradation products. SAM-e (and thus its enantiomers) must be further stabilized since it exhibits intramolecular instability that causes the destabilization and breakdown of the molecule at both high as well as ambient temperatures. SAM-e has therefore been the subject of many patents directed both towards obtaining new stable salts, and towards the provision of preparation processes that can be implemented on an industrial scale. The present patent thus envisions the use of any of the salts of SAM-e already disclosed in the prior art to stabilize the enantiomeric forms of SAM-e.

The clinical diagnostic field has seen a broad expansion in recent years, both as to the variety of materials of interest that may be readily and accurately determined, as well as the methods for the determination. Over the last several decades, testing for numerous substances such as drugs of abuse, or other biological molecules of interest has become commonplace. In recent years, immunoassay based on the interaction of an antibody with an antigen has been extensively investigated for this purpose. Based on the unique specificity and high affinity of antibodies, an immunoassay can accurately and precisely quantitate substances at the very low concentrations found in biological fluids.

Accordingly, there is a need for improved methods of detection and diagnosis of cancer and other diseases, as well as methods for monitoring the progress of the diseases and monitoring the progress of various treatments for cancer and other diseases by quantitating the methylating index as a biomarker.

SUMMARY OF THE INVENTION

Figure 1:
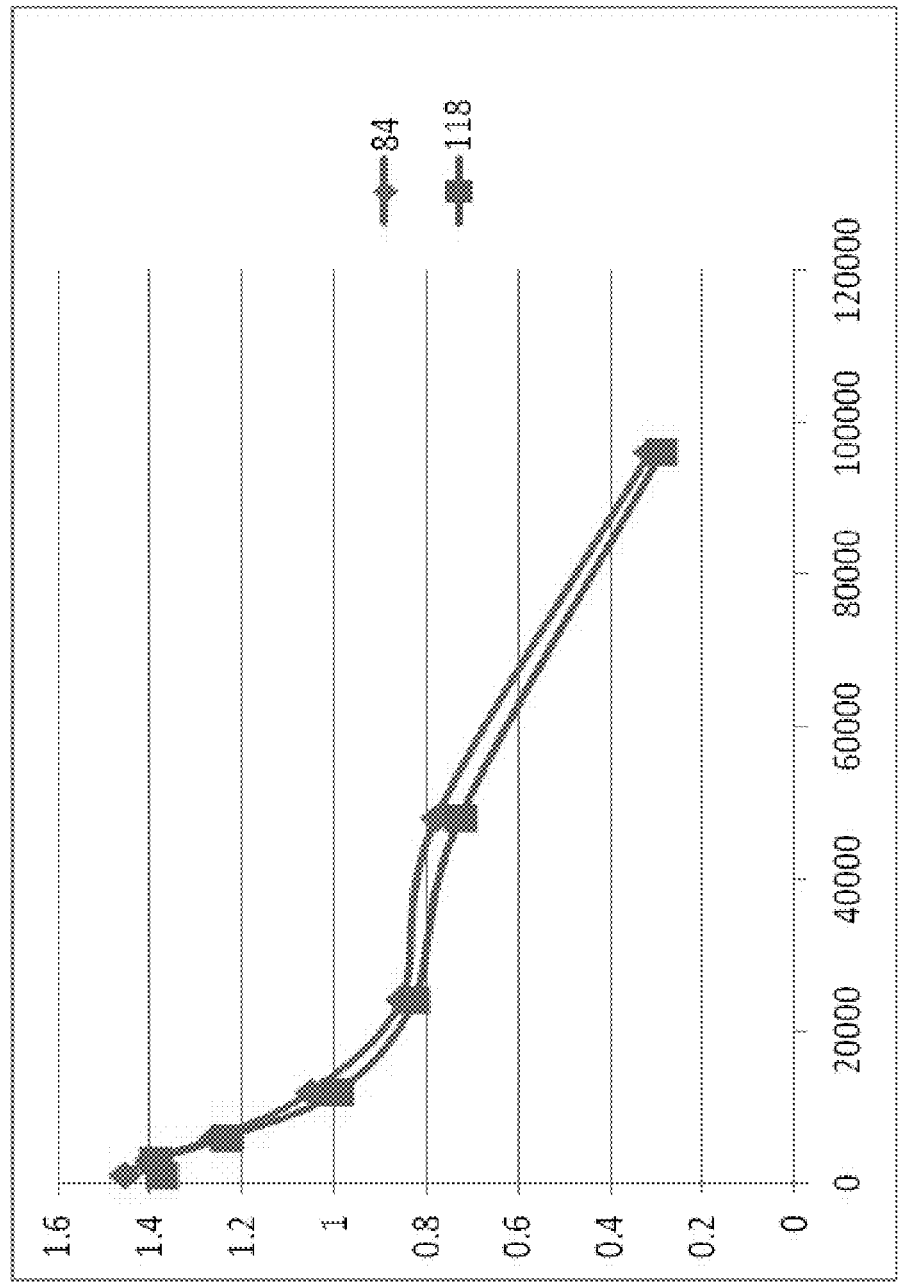
FIG. 1 shows the titers of two monoclonal antibody clones measured by ELISA. The y-axis shows the $OD_{450}$ values. The x-axis shows the dilutions of the purified ascites made at 1 µg/µl.

The instant invention provides a method for providing cancer therapy in a mammal afflicted with cancer which method comprises the following steps: (a) determining the methylation index in a biological fluid sample of said mammal afflicted with cancer; (b) correlating said methylation index to disease progression in said mammal; and (c) based on the results of (b) selecting the appropriate cancer therapeutic protocol to treat said mammal afflicted with cancer.

The methylation index is measured by a method comprising the following steps: (a1) determining the concentration of S-adenosylmethionine in said mammal wherein said method comprises: (i) obtaining a sample; (ii) mixing said sample with antibody specific for S-adenosylmethionine; (iii) detecting the binding of S-adenosylmethionine present in said sample with said antibody; (iv) quantifying the binding as a measure of the amount of S-adenosylmethionine present in said sample; (a2) determining the concentration of S-adenosylhomocysteine according to published literature procedures; and (a3) calculating the ratio of (a1)/(a2) to provide the methylation index of said biological sample.

The invention also provides a method for determining a cancer therapy regimen for treating a tumor in a patient comprising: (a) determining the methylation index in a patient sample; (b) comparing the level of methylation index obtained to a control methylation index to determine whether the level of said index is a predictive marker; and b) determining a cancer therapy regimen for treating the tumor based on the methylation index values, wherein the methylation index values are indicative that the patient is either a responsive patient or a non-responsive patient.

The invention is also directed to a method for treating mood disorders in a human which method comprises: (a) determining the concentration of S-adenosylmethionine in said human wherein said method comprises: (i) obtaining a sample; (ii) mixing said sample with antibody specific for S-adenosylmethionine; (iii) detecting the binding of S-adenosylmethionine present in said sample with said antibody; (iv) quantifying the binding as a measure of the amount of S-adenosylmethionine present in said sample; (b) correlating the levels of SAMe with said mood disorders; and (c) based on the correlation results of (b) administering effective amounts of a drug effective in treating said mood disorders.

The invention further provides a method for diagnosing in a subject, or predicting the susceptibility of a subject to, a mental or neurodegenerative disorder, the method comprising: (a) obtaining one or more biological samples from the subject; (b) determining the levels of S-adenosylmethionine or the methylation index associated with said sample; and (c) comparing the levels of the biomarkers determined in (b) with the levels of said biomarkers from one or more control samples, wherein abnormal levels of the two or more biomarkers in the sample(s) from the subject compared to the one or more control samples is predictive of susceptibility of the subject to a mental or neurodegenerative disorder.

The invention also relates to a method of detecting the presence or absence of a disease in a patient wherein said disease is accompanied by deficient levels of S-adenosylmethionine comprising: identifying a patient that is suspected of having said disease or is at risk of having said disease; obtaining a biological sample from said patient; determining the level of S-adenosylmethionine in said biological sample using an antibody derived from a hapten analog of S-adenosylmethionine; and correlating the level of S-adenosylmethionine in said biological sample with the presence or absence of said disease.

The invention is also directed to a method for assessing the need for treatment of a subject with S-adenosylmethionine alone or in combination with other chemotherapeutic agents comprising the steps of: (a) collecting a sample of body fluid from a subject suspected of needing such treatment; (b) measuring the amount of S-adenosylmethionine levels in said sample; (c) measuring the level of S-adenosylhomocysteine and calculating the methylation index; (d) comparing the methylation index of said sample with that of a normal standard; and (e) determining if the methylation index lies outside the normal range which is indicative of a need for S-adenosylmethionine treatment.

DETAILED DESCRIPTION OF THE INVENTION

The invention provides assays, diagnostics, therapeutics and medical evaluation of patients with a variety of diseases where it is necessary to asses their state of health. Their state of health can be assessed using assays that provide accurate concentration of S-adenosylmethionine and S-adenosylhomocysteine. Having accurate determination of the above molecules will allow for calculation of the methylation index which is an important parameter related to the state of health of a human being.

The assays of the invention uses antibodies which are specific to S-adenosylmethionine and analogs thereof and prepared by inoculating a host animal with an immunogen comprising an immunogenic substance directly or indirectly coupled to an S-adenosylmethionine hapten of the formula:

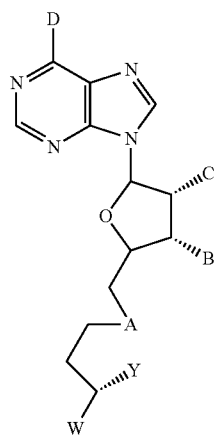

its enantiomers, diastereomers, enantiomerically enriched mixtures, racemic mixtures thereof, isotopically enriched forms thereof, crystalline forms, non-crystalline forms, amorphous forms thereof, charged and non-charged forms thereof, solvates thereof, metabolites thereof, and salts thereof; wherein A is selected from the group consisting of

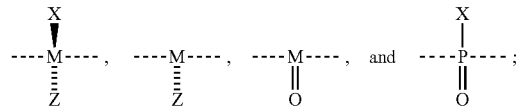

wherein M is selected from the group consisting of N, $N^+$, C, S, $S^+$, Se, $Se^+$, and P; ---- denotes the bonding location for each A group as defined above;

X is independently selected from the group consisting of H, $CH_3$, $CH_2OH$, $CH_2NH_2$, OH, $OCH_3$, $NH_2$, SH, CHO, and CN;

Z is independently selected from the group consisting of $CH_3$, $CH_2OH$, $CH_2NH_2$, OH, $OCH_3$, $NH_2$, SH, CHO, and CN;

B and C are independently selected from the group consisting of H, OH, $NH_2$, SH, F, Cl, Br, and I;

D is independently selected from the group consisting of $NH_2$, OH, SH, F, Cl, Br, and I;

Y is independently selected from the group consisting of H, $CH_3$, $CH_2OH$, $CH_2NH_2$, OH, $OCH_3$, $NH_2$, SH, CHO, and CN; and W is independently selected from the group consisting of H, COOH, $CONH_2$, $COOCH_3$, CN, CHO and functionalized derivatives thereof; and thereafter collecting serum from said host animal. The antibodies are described in detail in commonly owned U.S. Pat. No. 8,344,115, the entire contents of which are incorporated by reference as if it was denoted in its entirety.

In another aspect, the invention provides mouse monoclonal and rabbit polyclonal antibodies recombinant, humanized and chimeric antibodies against S-adenosylmethionine and against S-adenosylhomocysteine using the analogs as described in commonly owned U.S. Pat. No. 8,344,115.

The invention also provides immunoassays using monoclonal Anti-SAM and SAH antibodies to determine methylation index and the level of SAM in directing and developing SAM treatment regimen and general health evaluation, etc.

The invention further relates to using the methylation index as measured in the present invention as a screen marker in the general state of health of a given subject or population at large.

The instant invention further provides rapid, reliable and inexpensive immunoassay to measure SAM and SAH levels in urine, serum, plasma and whole blood semi-quantitatively are developed using rapid test strip devices. In an embodiment of the invention, a membrane is pre-soaked with anti-SAM (or anti-SAH) antibody-dye (colloidal gold) conjugate. Secondary antibody is immobilized in the Control zone. Anti-SAM (or anti-SAH) antibody is immobilized in Test zone. Specimen migrates along the membrane. If SAM (or SAH) is present, antigen-antibody complex is formed and will be captured by antibodies in both Test and Control zones, thus pink color is seen in both zones. If SAM (or SAH) is absent, antibody-dye conjugate is only captured by secondary antibody in the Control zone, thus pink band is seen only in control zone, which indicate test has worked correctly and the results from the test lines should be considered valid. Run standards and samples at the same time and compare the signal (color and width of the positive band) strength of test zones to those of standards to roughly determine the concentration of SAM (or SAH), a way to semi-quantify SAM (or SAH).

In a competitive immunoassay similarly as above, Test zone is immobilized with SAM (or SAH). The SAM (or SAH) from specimen competes with the SAM (or SAH) immobilized on Test zone to the limited amount of the antibody-dye conjugates. The more SAM (or SAH) there is from specimen, the less pink line will be seen from Test zone. Extremely low SAM (or SAH) or no SAM (or SAH) from specimen generates two strong lines in both Test and Control zones.

The semi-quantitative assay is ideal for consumers or patients to use before taking SAM-e as treatment for diseases, in the middle of SAM-e treatment, or to determine whether they should stop using SAM-e or not.

The invention also provides a method of personalized medicine for mammal diseases, the method comprising measuring the methylation index in body fluids from a subject having a disease, and proposing a treatment with a likelihood of being effective for said subject based on the methylation index levels in said body fluids.

The invention is also a method for monitoring the efficacy of a cancer treatment in a patient diagnosed with cancer comprising determining the methylation index level in the patient at a first point in time; treating the patient with a cancer treatment; determining the methylation index level in the patient at a second point in time; and comparing the level(s) of the methylation index in the subject at the first point in time with the levels at the second point in time to determine the efficacy of the cancer treatment.

In another aspect the invention provides a method for providing cancer therapy in a mammal afflicted with cancer which method comprises the following steps: (a) determining the methylation index in a biological fluid sample of said mammal afflicted with cancer; (b) correlating said methylation index to disease progression in said mammal; and (c) based on the results of (b) selecting the appropriate cancer therapeutic protocol to treat said mammal afflicted with cancer. The method includes collecting blood samples from patients having stage I, or stage II, or stage III, or stage IV cancer and determining the levels of SAM and SAH, then calculating the methylation index, correlating the methylation index with the cancer stage and then selecting an appropriate therapeutic protocol for treating said mammal.

The invention is also useful in determining how well and effective DNA methyltransferase inhibitors are in treating cancer. The methylation index is the best tool or means to help evaluate how, the extent and specificity of a certain DNA Methyltransferase (DNMT) inhibitors' functions in particular organs or tissues. Accordingly, the measurement of the methylation index can be used in assessing the effectiveness of DNA methyl transferase inhibitors by using the measurements developed as a result of the present invention.

The invention further provides:

1. Directed Therapies with SAMe

Both the effective studies on SAMe in treating mild to moderate depression, osteoarthritis (better than nonsteroidal anti-inflammatory drugs), fibromyalgia, and not so beneficial studies on SAMe have been reported. The most possible reason for this is similar to most other diseases and treatments, i.e. certain patients are not good candidates to use SAMe while some other patients are good candidates. To find out beforehand whether patients are good candidates for using certain medicine or not, some measurement has to be performed. Applicants' have discovered that it is desirable to determine the level of SAM in blood or urine samples before using SAMe for treatment of diseases.

Auxiliary treatment with SAMe in a variety of diseases, e.g. liver disorders, B12 or foliate deficiencies, cancers, Parkinson's patients who take Levodopa (L-dopa) has been accepted because these diseases can cause reduction of SAM level in the body. To be sure whether SAM level is actually reduced, the best way is to directly measure the level of SAM in blood plasma. There exist other situations when SAM level can be brought down due to therapies and diseases themselves. Therefore, monitoring SAM level is very important in improving overall efficacies of therapies whether the therapies include SAMe or not. For situations when SAM level is below certain acceptable level in the middle of other treatment regimen for depression, osteoarthritis, fibromyalgia, Parkinson's, Alzheimer's disease, dementia, liver disorders, bursitis, tendonitis, chronic low back pain, multiple sclerosis, spinal cord injuries, migraine headaches, lead poisoning, and to slow aging etc., supplementing appropriate dosages of SAMe will benefit overall treatment. For cases when treatment has not started, if SAM deficiency is detected, administering SAMe via IV for the diseases above would quickly relieve the symptoms.

On the other hand, as the information on drug or food interactions with SAMe is very limited, plus the fact that SAMe is not without risk of more significant psychiatric and cardiovascular adverse effects, consumers should be instructed to avoid unmonitored consumption of this dietary supplement until sufficient discussion has taken place with their primary healthcare provider (Fetrow, C. W. et al. "Efficacy of the dietary supplement S-adenosyl-L-methionine." Annals of Pharmacotherapy 35 no. 11 (November 2001): 1414-1425). Taking SAMe with prescription antidepressants can cause serotonin syndrome that can be quite dangerous. Immunoassay of SAM as describe in the U.S. Pat. No. 8,344,115 is the best way to allow clinical labs and patients themselves to quickly find out the level of SAM. The immunoassays described in the patent are sensitive, easy, quick, without using costly equipment. The results are comparable between assays. Furthermore, normal SAM concentration in plasma appears to be different, greatly depending on gender (normally, men>women), individual's weight, and maybe ethnicity, and diet, health condition, whether taking medicines or not, etc. Therefore, monitoring SAM level is critical in personalized and directed administration of SAMe to achieve the best result in treatment.

2. Methylation Index in Disease Development and Prognosis

Figure 6:
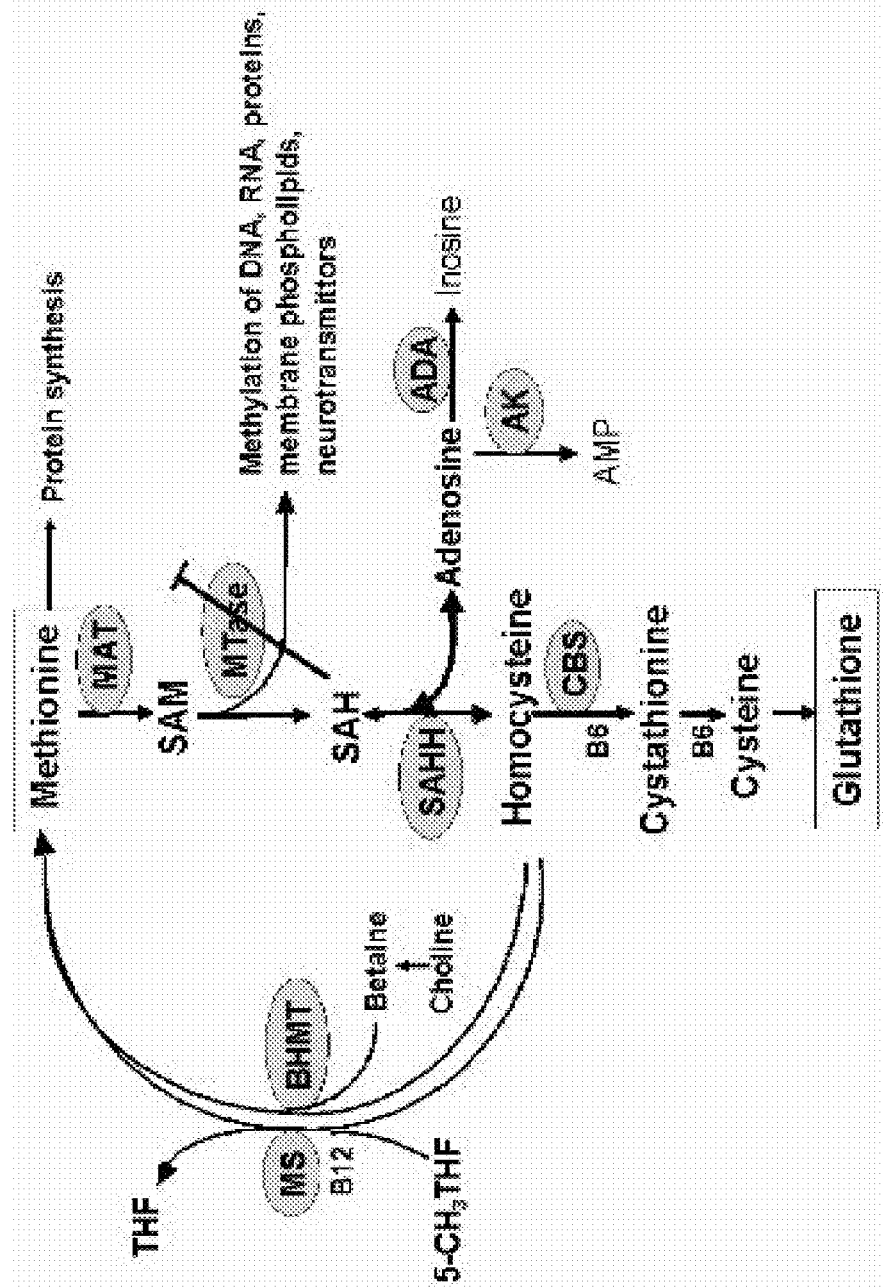
FIG. 6 illustrates the Methionine transsulfuration pathway. The abbreviations for the figure are: THF: tetrahydrofolate; MS: methionine synthase; BHMT: betaine-homocysteine methyltransferase; MAT: methionine adenosyltransferase; SAM: S-adenosylmethionine; SAH S-adenosylhomocysteine; SAHH: SAH hydrolase; ADA: adenosine deaminase; AK: adenosine kinase; CBS: cystathionine beta synthase.

The methylation index is defined as a ratio of concentration of SAM to concentration of SAH. It is important and more accurate to use methylation index instead of the level of SAM itself under certain circumstances. The reasons include (1) SAH+ is the direct end product of SAM methylation reaction after methyltransferase (COMT). The methionine transsulfuration pathway is depicted in FIG. 6. The SAHH is reversible enzyme whereas other enzymes are unidirectronal, the equilibrium dynamics of the SAHH reaction strongly favor SAH synthesis over homocystein synthesis (S J James, et al. Elevation of S-Adenosylhomocysteine and DNA Hypomethylation: Potential Epigenetic Mechanism for Homecysteine-Related Pathology. J. Nutri. 132:2361S-2366S, 2002). The accumulation of SAH inhibits activities of methytransferases, thus, reduces the level of SAM. The moment SAM as the sole donor of methyl group in cells provides methyl group to DAN, RNA, Protein, phospholipids, neurotransmitters, peptides, hormones, etc., SAH is produced. Therefore, the SAM/SAH is more sensitive and accurate in reflecting methylation reactions and an immediate and accurate indicator of methylation status/level of the important molecules in living organs especially when SAM fluctuation is subtle. (2) The level of SAM varies according to race, gender, body weight and diet, etc. Methylation index can reduce the variations caused by these and other factors.

Cancer is considered as both having genetics causes as well as epigenetic diseases. DNA methylation is one of the most important epigenetic modifications. More and more findings are being revealed on the importance of the once-neglected epigenetic influences on many life phenomena, which says the impact of methylation on cancers could be more and significant and in depth than what we know today. The level of DNA methylation in cancer cells varies in different stages of cancer development. Abnormal DNA methylation occurs commonly in cancers in a special format of genome-wide hypo-methylation and regional hyper-methylation. Global DNA hypo-methylation is associated with activation of proto-oncogenes, such as c-JUN, c-MYC, and c-Ha-Ras, and generation of genomic instability. Hyper-methylation on CpG islands located in the promoter regions of tumor suppressor genes results in transcriptional silencing and genomic instability. CpG hyper-methylation acts as an alternative and/or complementary mechanism to gene mutations causing gene inactivation, and it is now recognized as an important mechanism in carcinogenesis. The inactivation of tumor-suppressor genes (e.g. p53 gene) by CpG-island hyper-methylation of the CpG islands located in their promoter regions is related to the cancer progression and poor prognosis. Research results assign both therapeutic and chemo-preventive significance to methylation patterns in human Hepatocellular Carcinoma (HCC) and open the possibility of using molecular targets, including those identified in this study, to effectively inhibit HCC development and progression (Diego F. Calvisi et 1. "Mechanistic and Prognostic Significance of Aberrant Methylation in the Molecular Pathogenesis of Human Hepatocellular Carcinoma." J Clin Invest. 2007; 117(9):2713-2722).

Drugs that are meant to reduce the level of methylation of DNAs—demethylating agents, the promising chemotherapeutics drugs have been used and more are being studies to treat cancers (Esteller M. "DNA methylation and cancer therapy: new developments and expectations." Curr Opin Oncol. 2005 January; 17(1):55-60. 2005 January; 17(1):55-60).

In the context of the present invention, "cancer" or "tumor" is intended to include any neoplastic growth in a patient, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkins lymphoma). Solid tumors can originate in organs, and include cancers such as lung, breast, prostate, ovary, colon, kidney, and liver. As used herein, cancer cells, including tumor cells, refer to cells that divide at an abnormal (increased) rate. Cancer cells include, but are not limited to, carcinomas, such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endothelio sarcoma, lymphangio sarcoma, synovio sarcoma and mesothelio sarcoma; hematologic cancers, such as myelomas, leukemias (e.g., acute myelogenous leukemia, chronic lymphocytic leukemia, granulocytic leukemia, monocytic leukemia, lymphocytic leukemia), and lymphomas (e.g., follicular lymphoma, mantle cell lymphoma, diffuse large Bcell lymphoma, malignant lymphoma, plasmocytoma, reticulum cell sarcoma, or Hodgkins disease); and tumors of the nervous system including glioma, meningoma, medulloblastoma, schwannoma or epidymoma.

3. Methylation Index in Embryo Development and Overall Human Health

The levels of SAM and SAH may be involved in the control of somatic embryogenesis by affecting the level of DNA methylation, which in turn might cause differential changes in gene activation. An increase in the level of SAM may be a prerequisite for progression of embryogenesis and the development of complete embryos (Munksgaard D, et al. "Somatic embryo development in carrot is associated with an increase in levels of S-adenosylmethionine, S-adenosylhomocysteine and DNA methylation." Physiologia Plantarum, Volume 93, Issue 1, Article first published online: 9 OCT 2008).

Methylation Index in General Human Health Evaluation and Screening

The levels of SAM and SAH may be involved in the control of somatic embryogenesis by affecting the level of DNA methylation, which in turn might cause differential changes in gene activation. An increase in the level of SAM may be a prerequisite for progression of embryogenesis and the development of complete embryos (Munksgaard D, et al. "Somatic embryo development in carrot is associated with an increase in levels of S-adenosylmethionine, S-adenosylhomocysteine and DNA methylation." Physiologia Plantarum, Volume 93, Issue 1, Article first published online: 9 OCT 2008).

Methyltransferase (MT) plays an important role in human disease development. The Dopamine (DA) Hypothesis associated with the cause of Schizophrenia describes an overactive DA pathway in Schizophrenia patients. Catechol-O-methyltransferase (COMT) degrades DA in central nervous system. Inhibitors of COMT lay the foundation for treatment of Schizophrenia (Renson J et al "Action of the inhibitors of catechol ortho-methyl transferase on the adrenal catecholamines in the rat." Arch Int Physiol Biochim. 1960 May; 68:534-7). There are over 30 different kinds of MT that work on various substances critical to the functions of human being.

Methylation index is considered as an important indicator/marker for human general health, "vitality" indicators or "wellness" markers.

Furthermore, normal SAM concentration in plasma appears to be different greatly depending on gender (normally, men>women), individual's weight, and maybe ethnicity/race, and diet, etc. Similarly dependency exists for SAH concentrations since SAM and SAH are closely tied together metabolically. By utilizing the ratio of [SAM] and [SAH] it is likely these variables can be eliminated or diminished.

Connection of SAM and SAH to cardiovascular disease, depression, cancer and aging-related diseases such as Alzheimer's disease is well documented. Methylation is highly critical in fetus development, in differentiation, in epigenetic regulation of protein expression mainly via DNA, RNA and the histone methylation. The valuation of the S-adenosylmethionine and methylation capacity index is in their scientific basis as "vitality" indicators or "wellness" markers.

The invention is of particular importance as it provides:
1. Direct, accurate and quantitative measurement of methylation index with all types of bio-samples.
2. Direct, accurate and quantitative measurement of methylation index in all types of lab settings.
3. Direct, accurate and quantitative measurement of methylation index in relating to the evaluation of overall health conditions; cancer prediction and prognosis; treatment (with or without SAMe) evaluation of all diseases.
4. Direct, accurate and quantitative measurement of methylation index in relating to differential diagnosis of cancers.
5. Direct, accurate and quantitative measurement of methylation index in relating to chemotherapy resistance in cancer patients.
6. Direct, accurate and quantitative measurement of methylation index in relating to the evaluation of fetal development, differentiation and aging processes.
7. Semis-quantitative and qualitative immunoassay of methylation index with stripes or other media for use conveniently and easily by consumers in relating to reasons described in claims 1-6.
8. Semis-quantitative and qualitative immunoassay of SAM with stripes or other media for use conveniently and easily by consumers who take over-the-counter or prescribed SAMe for various situations and diseases.
9. Semis-quantitative and qualitative immunoassay of SAM with stripes or other media for use conveniently and easily by consumers with urine and blood samples.
10. Quantitative assay of SAM in relating to the directed medication of SAM-e for various reasons or purposes.

The invention also provides therapy with SAM-e and combination of SAM-e with multiple therapeutic drugs. The invention is intended to include compositions containing SAM-e and other therapeutic methods.

Figure 5:
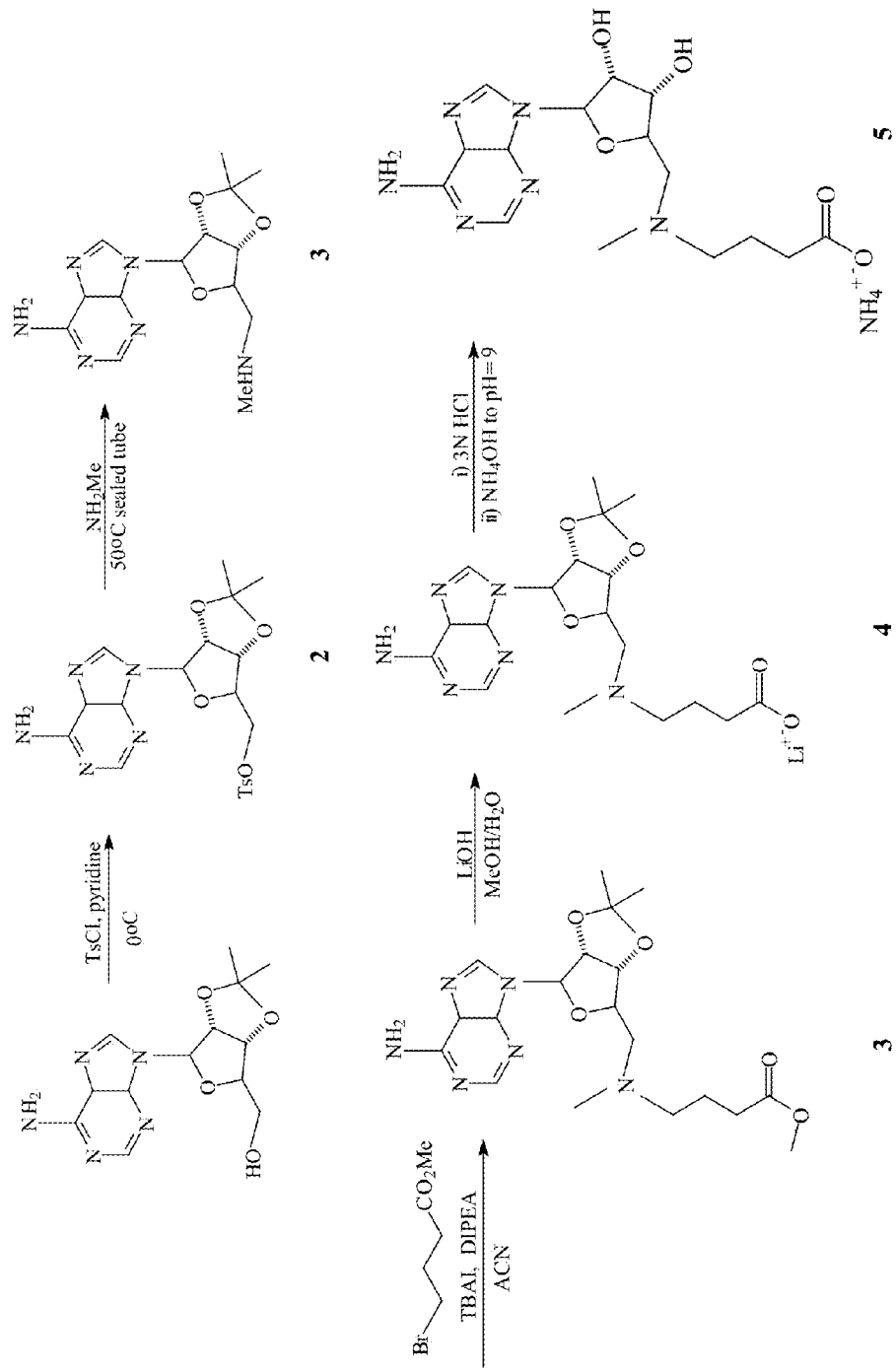
FIG. 5 shows the improved synthetic process of the invention for making hapten.

The present invention also provides an improved synthetic method for making the Azaadenosyl(deamino) methionine hapten which is used to make antibodies against SAM. The synthetic method is outlined in scheme 1 below and in FIG. 5.

Scheme 1

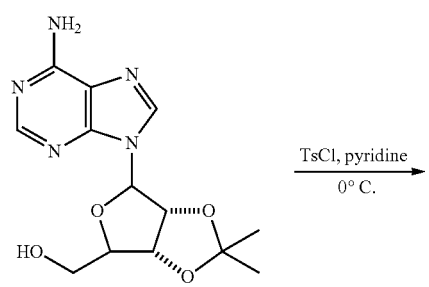

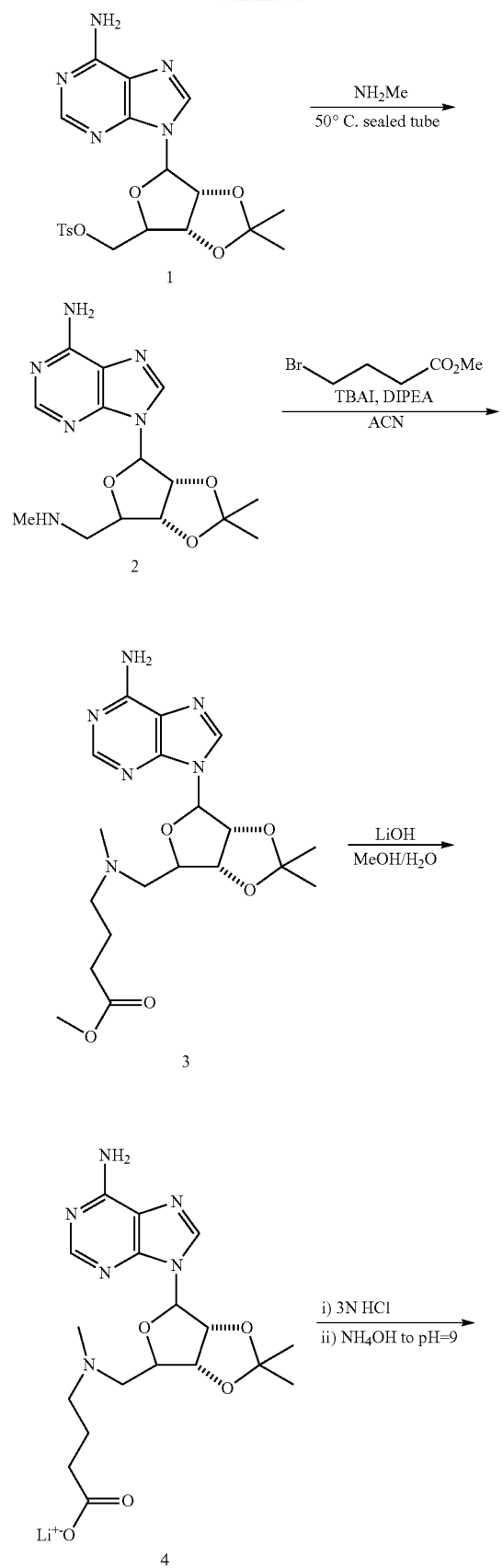

-continued

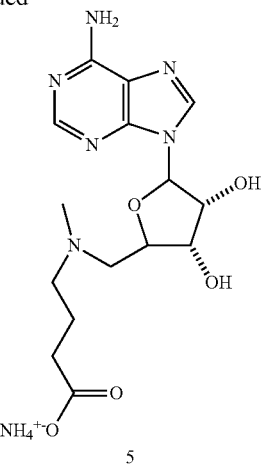

5

In carrying the method of the invention, blood samples are collected from patients having a given disease condition and analyzed for SAM and SAH levels using ELISA methods and antibodies generated according to the method of the invention. The ELISA Assay Format is as follows:

Format 1:

Sample or calibrator(s), (2) Antibody, (3) Hapten-Enzyme Conjugate, (4) Secondary antibody coated strips/microtiter plates, (Examples of secondary antibody: goat-anti-mouse antibody or goat-anti-rabbit antibody) (5) Wash solution, (6) Substrate(s). (7) Stopping reagent (optional if "end point" mode is used; for "rate" mode there is no need of a stopping reagent.)

Format 2:

(1) Sample or calibrator(s), (2) Antibody, (3) Secondary antibody-Enzyme Conjugate, (4) Immunogen (Hapten-carrier protein) coated strips/microtiter plates, (5) Wash solution, (6) Substrate(s and. (7) Stopping reagent (optional if end point mode is used; for "rate" mode there is no need of a stopping reagent.

Format 3:

(1) Two paired antibodies against two different epitopes of a molecule, (2) Sample or calibrator(s), (3) One antibody in (1) is conjugated with enzymes. (4) Wash solution, (5) Substrate(s). (6) Stopping reagent (optional if "end point" mode is used; for "rate" mode there is no need of a stopping reagent.)

The present invention also provides test kits which are based on an immunoassay (e.g., the ELISA test) for the immunological detection of SAM which contain in addition to antibody against S-adenosylmethionine. The ELISA test kits can be in the any of the ELISA formats above. For example, the following components: (a) secondary Ab attached to solid phase; (b) immobilized hapten, hapten derivative, immunogen or alike; (c) enzyme substrate(s) in solid or dissolved form; (d) labeled hapten or derivatives (tracer or enzyme conjugates); (e) buffering and washing solutions; (f) additives to prevent, for example, nonspecific adsorption and aggregation; and (g) pipettes, incubation vessels, reference standards, calibration curves, and color tables.

Once the levels of SAM and SAH are determined, the methylation indeces are calculated and used to determine the state of health of the individual.

Generally speaking the average levels of SAM in healthy individuals was about 147±16 nM, the SAH level was 29±11 nM based on measurements from 11 healthy individuals. The methylation index was 5±1. The normal methylation index is above 4.

The average level of SAM for cancer patients was 103±52 nM

The average level of SAM was 113±15 nM on patients with atherosclerosis. Preliminary results from SAH quantitative ELISA using rabbit monoclonal antibody against SAH showed substantially higher levels for SAH therefore, the SAM/SAH is reduced significantly in patients with Arthero-sclerosis.

The average level of SAM in plasma is 45±8 nM (from 26 samples) for patients with liver disorders and therefore much lower than that of normal people.

The ratio of SAM and SAH level is calculated and called methylation index, which is a more accurate and convincing measure to evaluate general health, disease status, development and prognostics than a single value of either SAM or SAH. Normally the methylation index is >4. In some pathological situations, it is less than 4 or even less than 1 due to decreased SAM level and increased SAH level. The reduced methylation index in turn will affect the methylation processes of many important molecules such as DNA, RNA, peptides, hormone, neurotransmitters, etc.

The methylation index is used to determine a chemotherapeutic protocol. Cancer patients with significantly reduced methylation index levels are treated with more aggressive protocols. The methylation index is correlated with the stage of the cancer to select an appropriate therapy for each patient.

EXAMPLES

The following examples are intended to demonstrate the usefulness of the methods and therapeutic compositions of the present invention and should not be construed to limit the scope of the invention in anyway.

Example 1

Generation of Monoclonal and Polyclonal Antibodies Against SAM and SAH

Reagents:
AdaM: Azaadenosyl(deamino)methionine
ASAM: Aza-SAM, or Nitrogen (N)-adenosylmethionine
BgG: Bovine gamma globulinBSA: Bovine serum albumin
BTG: Bovine thyroglobluinCSAM: Carbon (C)-adenosylmethionine or 6(s)-Methyl-6-deaminosinefungindaH: Deamino-5-adenosylhomocysteinedaHSO:daH sulfoxide
DCC:N,N'-dicyclohexylcarbodiimide
DMF: Dimethylformamide
EDAC: 1-Ethyl 3-(3-Dimethylaminopropyl)carbodiimide
ELISA: enzyme-linked immunosorbant assay GAM plate/strip: goat-anti-mouse IgG coated microplate or stripGAR plate/strip: goat-anti-rabbit IgG coated microplate or stripHRP: horse radish peroxidaseIB: Incubation buffer-
KLH: Keho lympet hemocyanine
NHS: N-Hydroxysuccinamide
PBS: phosphate-buffered saline
RT: retention time (for HPLC) or room temperature
SAH: S-Adenosylhomocysteine
SAM: S-Adenosylmethionine 1. Preparation of AdaM-NHS: To a flask containing overnight vacuum-died AdaM (15.1 mg, ca. 0.041 mmole) was added 21.7 mg (0.107 mmole) of DCC and 7.2 mg (0.061 mmole) NHS. The solid mass was left on vacuum line for 3-4 hr drying. Approximately 1.5 mL dry DMF was then added to the flask under nitrogen atmosphere, and then seal the flask. The solution was stirred at RT overnight. TLC (10% MeOH in CH2Cl2) analysis indicated the formation of the NHS ester.

2. Preparation of AdaM-BSA: Weighed out 59.8 mg BSA to a round bottomed flask and added 5 ml freshly prepared 100 mM sodium phosphate solution, pH 8.25. Place the BSA solution in a 4° C. water bath with vigorous stirring. The AdaM-NHS prepared as described above was then slowly added in 10 µl aliquot every few minutes. After a total of 150 µl was added, the conjugation mixture became turning cloudy. One milliliter of DMSO solution was added to aid dissolution. Upon addition of another 50 µl AdaM-NHS in DMF, the mixture turned cloudy again. Water bath sonication was then applied for 5 minutes after every 10 µl×5 of AdaM-NHS was added. At the conclusion of 150 µl in total of AdaM-NHS in DMF was added, the mixture was sonicated for 20 minutes. To insure the conjugate was free from any hapten, the pool was dialysis against PBS (1.5 liter×4) over 2 days. The final volume of the conjugate is approximately 36 ml, at estimated 1.66 mg/ml BSA.

3. Preparation of AdaM-KLH: Using the method above, weighed out 17.5 mg KLH, AdaM 15.1 mg. The final volume after dialysis is 29.5 ml with concentration of 0.6 mg/ml.

4. Preparation of AdaM-PLL: AdaM 4.72 mg was dissolved in 1 ml DMF, EDC.HCl 6.5 mg and NHS 4.0 mg were added, then the mixture was well-sealed, stirred at room temperature in dark overnight. Weighed out 1.5 mg PLL dissolved with 1 ml 10 mM PBS pH 8.2. The activated AdaM was then added slowly to the PLL solution and the mixture was left overnight in dark. Dialyzed the reaction mixture for 48 hours with 10 mM PBS pH 7.3. The final volume after dialysis is 3.5 ml with concentration of 1.4 mg/ml.

5. Preparation of SAH-BSA: SAH (Sigma) 3.8 mg was dissolved in 1.5 ml DMF, EDC.HCl 10 mg and NHS 4.5 mg were added, the mixture was well-sealed, stirred at room temperature in dark for 24 hours. Weighed out 12.9 mg BSA dissolved with 2 ml 10 mM PBS pH 7.8. The SAH solution was added slowly to the BSA solution and the mixture was left at 4° C. in dark overnight with stir. Dialyzed the reaction mixture for 72 hours with 10 mM PBS pH 7.3. The final volume after dialysis is 8.4 ml with concentration of 1.4 mg/ml.

6. Preparation of SAH-PLL: SAH 1.5 mg was dissolved in 1 ml DMF, EDC.HCl 4 mg and NHS 2 mg were added, then the mixture was well-sealed, stirred at room temperature in dark overnight. Weighed out 1.5 mg PLL dissolved with 4.7 ml 50 mM PBS pH 9.6. The activated SAH was then added slowly to the PLL solution and the mixture was left overnight in dark. Dialyzed the reaction mixture for 48 hours with 10 mM PBS pH 7.3. The final volume after dialysis is 7.0 ml with concentration of 0.93 mg/ml.

7. General Procedure for generating monoclonal antibodies against SAM and SAH:

Mouse monoclonal production is a common practice, based on the procedure developed by the pioneer work of Kolher and Milstein (Nature, 256, 495-497, 1975).

Balb/c mice were used for monoclonal antibody immunization and ascites production. Immunization (1 ml total volume) was carried out with subcutaneous injections at multiple sites. Initial injection utilizes 1:1 mixture of complete Freund Adjuvant and AdaM-BSA as well as AdaM-KLH conjugate solutions in PBS upon emulsification. Subsequent injections use incomplete Freund adjuvant.

Blood was collected periodically from immunized animals and cells were removed by centrifugation. Antisera thus obtained were then evaluated to determine the immune response and the antibody titer. Depending on application, antibody may be used directly. When necessary, they can be further purified to immunoglobulin level with ammonium sulfate or sodium sulfate or by protein A column chromatography, etc.

For monoclonal antibody, once the clone is obtained it can be injected into host for ascites production. Antibody was then purified from the ascites fluids by protein A affinity column. The hybridoma clone can also be cultured on hollow fiber method to produce antibody.

Mice was primed with intravenous injection of immunogen three days prior to its termination. The spleen of the mouse was harvested and homogenized with a French Press. The spleen cells were then fused with myeloma NS-1 cells in 5:1 ratio. The fused cell suspension was then plated out on 96 wells microtiter plates. The hybridoma were grown on RPMI1640 enriched with 18% fetal bovine serum, HAT and HT supplement, and screened. Clones that are positives to AdaM-PLL conjugate were selected for further studies. Final selection was based on assay performance and cross activity profile. Selected clones were then injected into mice to produce ascites fluid.

Through serial screening and selection, we identified a few clones that have a better specificity and less cross reaction with other analogs. The titers of two monoclonal antibodies are tested and the results were shown in FIG. 1:

8. Rabbit Polyclonal Antibodies Against SAM and SAH

New Zealand White rabbits were used for polyclonal antibody production. Immunization (1 ml total volume) was carried out with subcutaneous injections at multiple sites. The immunization process is the same as when immunizing mouse for monoclonal production. The rabbit antiserum was test and the titer was above 1:12000 for both anti-SAM and anti-SAH seria before seria were collected Example 2

Antibody Specificity

Figure 2:
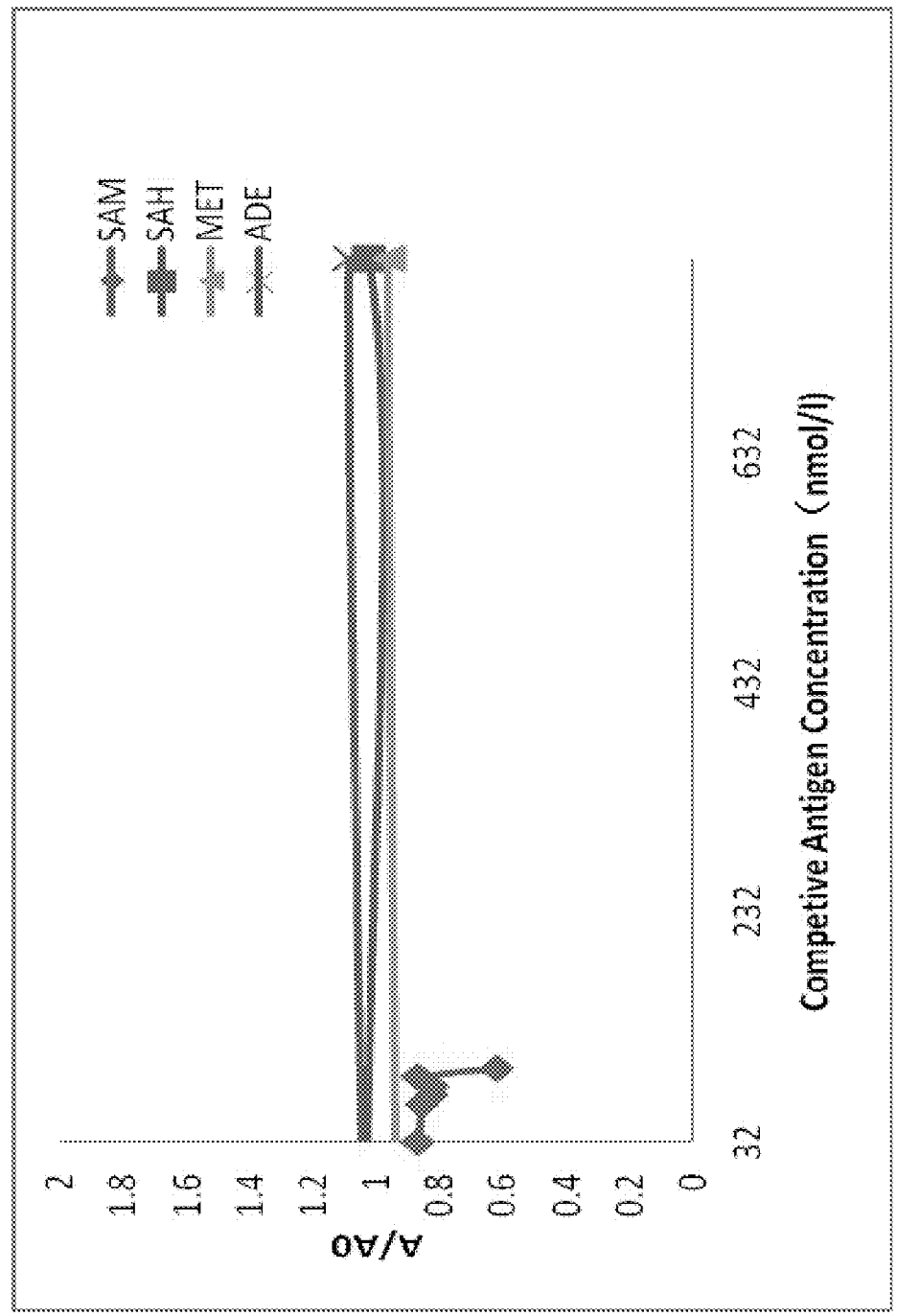
FIG. 2 describes a different competitive analog and SAM were added and the cross reaction of the clone #84 was measured at less than 1.25%. The x-axis shows a part of the concentration of SAM and analogs used and they are in nM. A sample of the subject hybridoma clone #84 (as subclone 84-3) was deposited at the China Center For Type Culture Collection (CCTCC) Address: Wuhan University, Wuhan Zip code: 430072 on Sep. 16, 2017, and has been assigned the CCTCC number C2017178.

To further test the specificity of the clones, cross reactions of clone #84 (Deposited as subclone 84-3 at the China Center For Type Culture Collection as number C2017178) is very low, <1.25% (See FIG. 2). Three analogs used in the cross reaction are SAH, methionine and adenosine. About 80 folds higher dosages of analogs than that of SAM was used in competitive ELISA. At 10 µM dosage of the SAH, methionine and adenosine, competition of coated antigen did not occur. However, no inhibition was seen by three analogs, the inhibition was clearly seen when SAM was added at a much lower dosage than those of the analogs, and the inhibition by SAM could easily go higher than about 40% that was seen in this experiment, as can been seen from FIG. 2.

Figure 3:
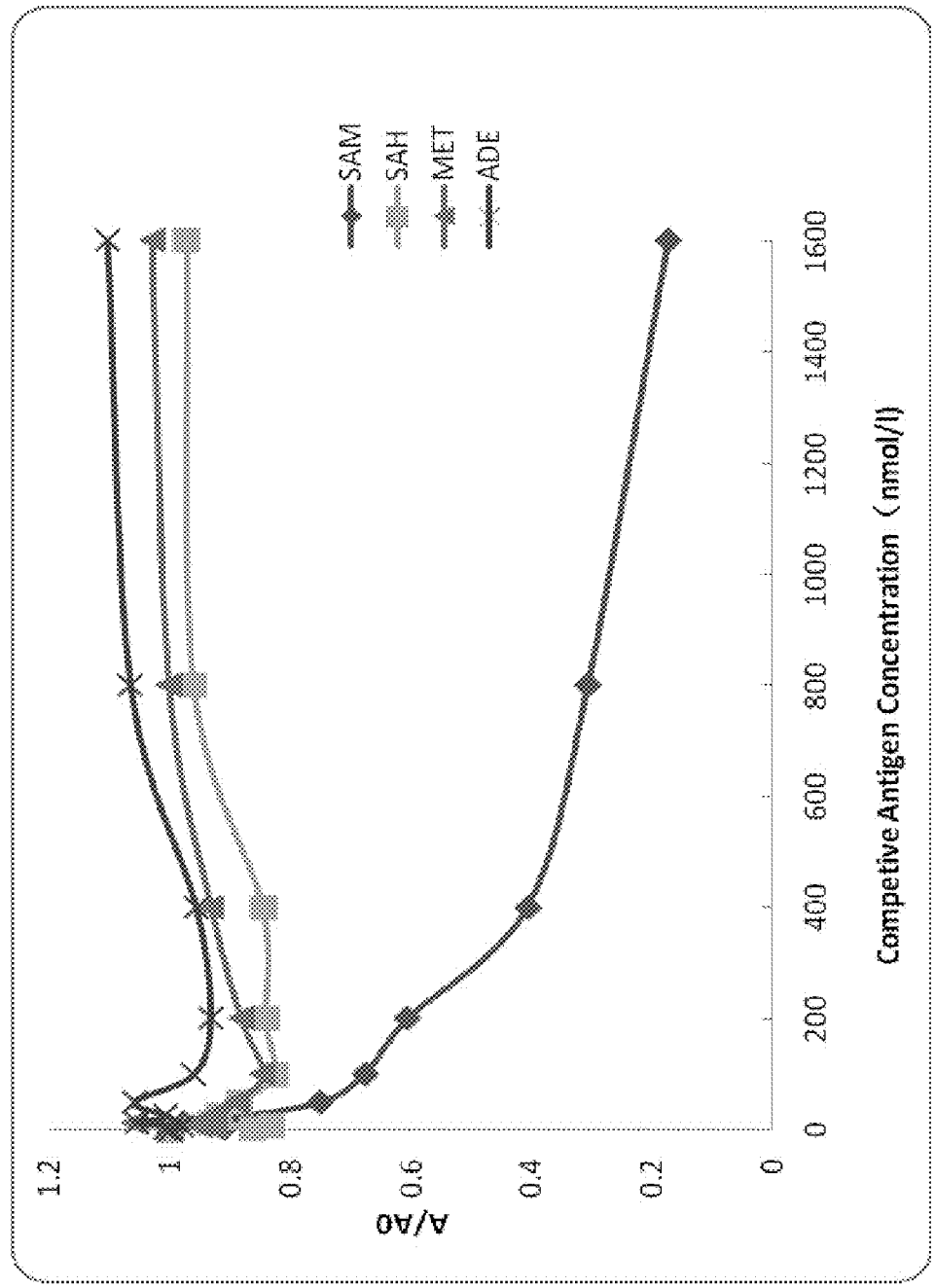
FIG. 3 features the different inhibition capabilities of SAM, SAH, methionine and adenosine observed in the competitive ELISA assay using micro-titer plate coated with AdaM-BSA. The y-axis shows the A/A0 that is the ratio of each $OD_{450}$ value and the blank well (after background subtraction).

Cross reactions of clone #118 (deposited as subclone 118-6 on Sep. 16, 2017 at the China Center For Type Culture Collection as number C2017179) with SAH, methionine and with adenosine is also very low (FIG. 3). The same dosage of SAM, SAH, methionine and adenosine were used in the competitive ELISA. The result showed that free SAM significantly inhibited the binding of the monoclonal anti-SAM antibody to the AdaM-coated micro-titer plate, whereas SAH, methionine and adenosine did not.

Example 3

Competitive ELISA Assay

Reagents:

IB: 10 mM phosphate, 150 mM NaCl, 0.2% BSA, 0.1% Tween 20, 0.1% Proclin, pH 7.4. Samples: (a) SAM toluenesulfonate (tosylate) disulfate (Sigma) (b) SAH sodium (MW 406.39) (c) Adenosine (Sigma) (d) Methionine (Sigma). HRP-Goat-Anti-Mouse IgG (H+L) (EarthOx, San Francisco, Calif.). HRP substrate: one reagent substrate solution NeA-blue Tetramethyl-benzidine Substrate. Antigen dilution buffer: IB with 0.5% BSA. Coating buffer: 50 mM carbonate butter pH 9.6. Washing buffer: PBS, pH 7.5, 0.1% Tween-20.

(1). AdaM-BSA coated micro-plate was blotted, decanted and then competitive SAM, SAH, methionine and adenosine were added in 40 μl antigen dilution butter. The 44 μl of 0.025 μg/ml purified monoclonal antibody against SAM and 16 μl of IB+Tris (100 mM) buffer, pH 8.5 was added and together incubated at 37° C. for 1-2 hours.

(2). The micro-titer plate was washed three times with PBST and blot dry.

(3). To each well was then added 100 μl of properly diluted HRP-goat-anti-mouse antibody and incubated at 37° C. for 20 minutes.

(4). The assay mixture was then decanted, washed, and blot dry.

(6). To each well was added 100 μl/well of HRP substrate and incubate for 10-15 min.

(7). Stop the substrate development with 50 μl/well of 2N $H_2SO_4$.

(8). $OD_{450}$ was recorded.

In order to quantify the amount of SAM in bio-samples, competitive ELISA was developed.

Figure 4:
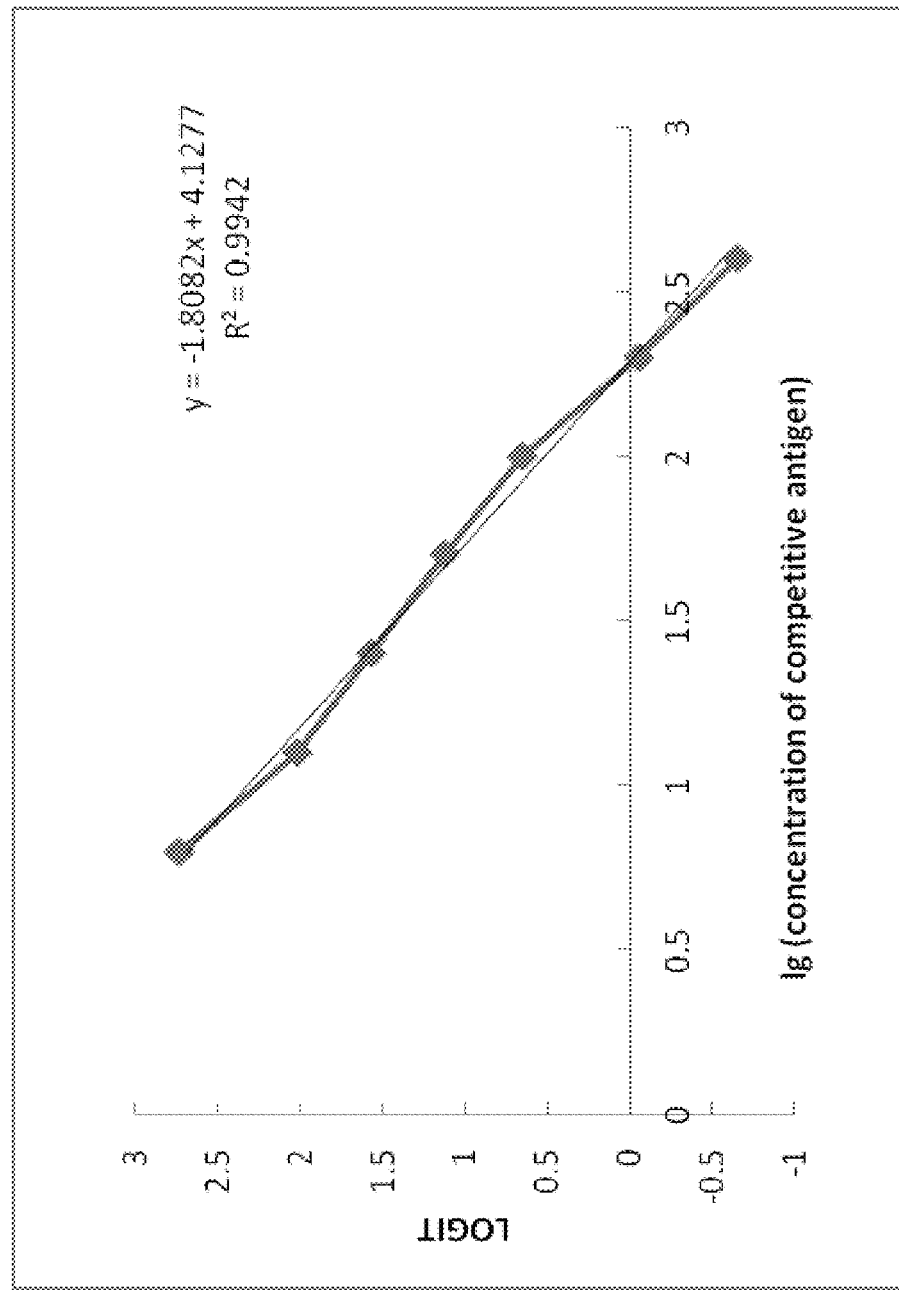
FIG. 4 is the standard curve for ELISA for SAM quantification. The x-axis is logarithmic value of SAM concentration. The y-axis is the LOGIT value.

The standards curve for competitive ELISA of SAM and SAH in competitive ELISA is shown in FIG. 4.

The LOGIT is defined as $Ln(A/A0)(1-A/A0)$ where A is the $OD_{450}$ value of a sample or the standard, A0 is the $OD_{450}$ value of the control well. The negative LOGIT value indicates that A/A0 is less than 50% and inhibition rate (1−A/A0) is over 50%, which is an abnormal situation that should not be evaluated normally.

The standard in the amount of 12.60 mg is accurately weighed and was dissolved in small amount of DMF and then thoroughly dissolved in 0.1 mM HCl with 250 ml flask. From it, the 5 μg/ml. 2.5 μg/ml, 1.25 μg/ml, 0.625 μg/ml, 0.3125 μg/ml and 0.15625 μg/ml standard solutions were made in 100 ml flasks respectively.

Example 4

HRP-conjugated monoclonal antibody from clone #84 (deposited as subclone 84-3 at the China Center For Type Culture Collection as number C2017178) was made. Another monoclonal antibody clone is paired with clone #84 (deposited as subclone 84-3 at the China Center For Type Culture Collection as number C2017178) so that sandwich ELISA is to be established to quantify SAM level.

Example 5

Blood Sample Collection Procedure

Blood samples were obtained from normal people and patients with consent. Peripheral venous blood was drawn into tubes with EDTA. The tubes were cooled immediately at 4° C. and centrifuged at or above 2000 g for 10 minutes within 30 minutes after blood collection to obtain plasma. About 10 μl 1N acetic acid was added into 100 μl plasma for samples to be measured for SAM and SAH. The plasma was either used in measurement or frozen under −70° C. for future use. The aliquots of the whole blood cells after plasma removal were also made for measuring SAM and SAH or making DNA. In some situations, white blood cells were isolated from the whole blood cells and frozen for future DNA extraction.

Example 6

The blood SAM and SAH samples from 11 normal people aged 20 to 50 Asian males and females with normal build were measured with direct competitive ELISA assay as described above. The average value for SAM was 147±16 nM. The SAH level was 29±11 nM. The methylation index was around 5±1. More samples are being collected and the SAM and SAH values detected by immunoassay will be used to perform large-scale studies on SAM and SAH levels in blood plasma in terms of different race, age, gender, body weight, diet, life style, etc. As large scale epidemiological studies on SAM/SAH are carried out, compared with various disease situations described below and in the body of this invention, it is likely to use methylation index as a brand new general health indicator.

Example 7

Blood samples were obtained from cancer patients who were hospitalized for chemotherapy. The samples were measured with direct competitive ELISA assay for SAM and SAH levels. The average level of SAM for cancer patients was 103±52 nM, and the SAH level was 250±90 nM from 12 samples. The average methylation index was less than 0.5. More samples and observations with diagnostic details, symptoms, cancer stages, progression, treatment, relapse and prognostic information are being conducted to generate a complete profile of the human methylation index and its relationship to various aspect of cancer at different levels. Blood samples are also collected from various patients with other types of cancers before and after chemotherapy. The DNA methylation level will be measured from the white blood cells as well. The relationship between particular DNA methylation disorders from cancer patients and methylation index or DNA global methylation is also expected to provide further impact on state of health and therapeutic protocols.

Example 8

Blood plasma were obtained from patients having Atherosclerosis disorders and heart attack (patients from Intensive Care Unit) and then analyzed for SAM, SAH with direct competitive ELISA assay as well as homocysteine (using commercial ELISA kit). The average level of SAM was 113±15 nM and SAH was 680±258 nM as detected from blood samples from 10-such patients. Preliminary results from SAH quantitative ELISA using rabbit monoclonal antibody against SAH (ab111903 from abcam, Cambridge, Mass.) level in heart attack patients showed significant increase. More data are being generated to show SAM/SAH is reduced significantly in patients with atherosclerotic vascular disease in the coronary, cerebral, and peripheral vessels as well as the its relationship to the level of homocysteine that was considered as a predictor of cardiovascular mortality. SAM/SAH may be a better and direct indicator than homocysteine in the evaluation of potential outcomes of heart attack and its therapeutic efficacy.

Example 9

Blood samples were obtained from patients having liver disorders such as contagious hepatitis (some accompanying ile problems including Cholestasis), liver cirrhosis, fibrosis and then analyzed for SAM and SAH levels with direct competitive ELISA. The average level of SAM in plasma was 45±8 nM from 26 samples. The level of SAM in liver disorders was much lower than that of normal people. The SAH level was 342±129 nM, however, higher than that of normal people. The methylation index was about 0.13.

Example 10

Blood samples were obtained from patients having been diagnosed as depression and then analyzed for SAM as follows:

Blood samples from depressed patients will come from The Second Xiangya Medical College Hospital Psychiatric Institute of Health for those depressed patients without obvious organic damages or diseases, as well as from The Second Ningbo Hospital Neurology Department and Rehabilitation Department for those depressed patients with some organic diseases. We especially compare SAM and SAH levels in depressed patients who take SAM-e or other medicines before and after treatment of depression. The level of SAM was 20±18 nM and SAFE was 340±180 nM from 10 samples. The methylation index was around 0.064.

SAM or methylation index can be a good indicator to personalize depression therapy and aids in prognostic prediction. Qualitative and semi-quantitative SAM rapid test strips are convenient choices available for patients who need to decide whether to take SAM-e or other anti-depression medicines. This helps direct patients to choose the medicines that best fit them.

Example 11

Blood samples were obtained from patients with Parkinson's disease and then analyzed for SAM as follows:

Blood samples from The Second Ningbo Hospital Neurology Department and Rehabilitation Department who are diagnosed as Parkinson's disease are included in the study. The levels of SAM and SAH from the plasma are measured using the immunoassays developed in this invention.

Example 12

Blood samples were obtained from patients with Rheumatoid arthritis and multiple sclerosis, and then analyzed for SAM as follows:

Blood samples from The Second Ningbo Hospital Neurology Department and Rehabilitation Department who are diagnosed as osteoarthritis diseases or multiple sclerosis are included in the study. The levels of SAM and SAH from the plasma are measured using the immunoassays as described above. Research is conducted on how SAM or methylation index changes with osteoarthritis and multiple sclerosis. The levels of SAM and SAH are compared in osteoarthritis and multiple sclerosis patients who take SAM-e or other medicines before and after treatment of osteoarthritis and multiple sclerosis. SAM or methylation index is a good indicator to personalize osteoarthritis and multiple sclerosis therapy and aids in prognostic prediction Qualitative and semi-quantitative SAM rapid test strips are convenient choices available for patients who need to decide whether to take SAM-e or other medicines for osteoarthritis and multiple sclerosis problems. This helps direct patients to choose the medicines that best fit them.

Example 13

The methylation indexes of the samples used in Examples 6 to 12 were done as follows: Using the immunoassays developed in this invention to measure SAM and SAH at the same time. The ratio of SAM and SAH level is calculated and called methylation index, which is a more accurate and convincing measure to evaluate general health, disease status, development and prognostics than a single value of either SAM or SAH. Normally the methylation index is >4. In some pathological situations, it is less than 4 or even less than 1 due to decreased SAM level and increased SAH level. The reduced methylation index in turn will affect the methylation processes of many important molecules such as DNA, RNA, peptides, hormone, neurotransmitters, etc.

Example 14

Compound 1: 2',3'-O-Isopropylideneadenosine (25 g, 82 mmol, 1 equivalent) and dry pyridine (200 mL) were placed into a single neck, 500 mL round bottom flask along with a magnetic stir bar then placed under nitrogen atmosphere. The flask was then heated with a heat gun while stirring vigorously. After approximately 5 minutes all solids dissolved. Once in solution, the mixture was cooled in an ice-water bath and stirred for 20 minutes. Tosyl-CI was added as a solid in 8 small portions over I hour to prevent a significant exotherm. The mixture was kept at 0° C. for 5 days. Once the reaction was complete by TLC, the mixture was diluted with 100 mL H20 and 300 mL of ethyl acetate. The mixture was transferred to a separatory funnel and 100 mL of 3N HCl was added. The layers were separated and the organic layer was washed with five 200 mL portions of water to remove excess pyridinium hydrochloride. The organic layer was concentrated under reduced pressure then the residue was taken up in 100 mL of dichloromethane. This was slowly added to a stirring solution of heptane (1.12 L) via addition funnel. The off-white precipitate was filtered off to give 31.1 grams of pure product confirmed by mass spec and IH NMR.

Example 15

Compound 2: Compound 1 (32.2 g, 70 mmol) was added to a 300 mL sealed tube along with a magnetic stirbar. Around 200 mL of a 2M solution of methylamine in THF was poured into the tube and the tube was sealed. The vessel was submerged into a 50° C. oil bath then stirred for two days. The reaction vessel was taken out of the oil bath and then placed into an ice-water bath and stirred for 30 minutes. The cap was then removed and the excess methylamine was blown out by sparging with a gentle stream of nitrogen. The residue was then transferred to a round bottom flask and concentrated under a reduced pressure. The gum-like residue was purified by flash column chromatography (5% MeOH in DCM) to give 3.51 grams of 2. The structure was confirmed by I H NMR.

Example 16

Compound 3. Amine 2 (5.0 g, 15.6 mmol, 1 equivalent) was placed into a single necked 500 mL round bottom flask.

150 mL of dry acetonitrile was added followed by diisopropylethylamine (2.1 g, 16.38 mmol, 1.05 equivalents) and stirred at 35° C. for 30 minutes. Bromobutyrate (2.55 g, 14.1 mmol, 0.9 equivalents) was added drop-wise via syringe, followed by tetrabutylammonium iodide (288 mg, 0.78 mmol, 5 mol %). The mixture was stirred at 40° C. for 5 days. The reaction mixture was then concentrated under reduced pressure and purified by flash chromatography (5% MeOH in DCM) to provide 5.36 grams of the desired product in 82% yield.

Example 17

Compound 4. Methylester 3 (7.76 g, 18.4 mmol, 1 equivalent) was placed in a 250 mL round bottom flask and taken up in 15 mL of methanol and 15 mL H20 and stirred for 10 minutes. Solid lithium hydroxide (1.55 g, 36.8 mmol, 2 equivalents) was added and the mixture was stirred for approximately 2 hours (until TLC and LCMS showed the complete disappearance of starting material). The crude mixture was concentrated to dryness and then carried on to the next step without further purification.

Example 18

Compound 5: Approximately 7 grams of the crude lithium salt 4 was dissolved 150 mL of 3N HCl and stirred at ambient temperature for 4 hours (until starting material completely disappeared on TLC and LCMS). The crude mixture was filtered through filter paper then concentrated to dryness under reduced pressure. The crude residue was purified in 5 portions on a 120 gram reverse phase column eluting the product at a gradient of 40% methanol in water. The purified fractions were pooled and then concentrated to dryness under high vacuum at 40° C. The product was a brown foam that collapsed back to a brown oil upon standing. The product was confirmed by HPLC. MS. and IH NMR. 4.8 grams of 99.55% pure (HPLC) product was then divided and transferred into 9 vials with a 1:1 mixture of methanol and water. Each sample was then concentrated to dryness under high vacuum at 40° C. until the mass remained constant.

All patents, patent applications and journal publications cited in this application including all cited references in those applications, are hereby incorporated by reference in their entirety for all purposes to the same extent as if each individual patent, patent application or publication were so individually denoted.

While the many embodiments of the invention have been disclosed above and include presently preferred embodiments, many other embodiments and variations are possible within the scope of the present disclosure and in the appended claims that follow. Accordingly, the details of the preferred embodiments and examples provided are not to be construed as limiting. It is to be understood that the terms used herein are merely descriptive rather than limiting and that various changes, numerous equivalents may be made without departing from the spirit or scope of the claimed invention.

Example 19

Patients with stage 1 cancer are examined and their SAM levels and SAH levels are measured and the methylation indeces are calculated. Pateints with methylation indeces of less than 2 are started with SAM once a day while they are undergoing chemotherapy.

Example 20

Measuring methylation index from urine (or blood sample if urine cannot be used normally because of some specially components in it or the concentration of SAM in urine is too low) is a good way to personalize depression therapeutics. SAMe therapeutical protocol may look like this:

For adult patients, depending on the severity of the mood and other health problems, many regimens have been used, for example:

Daily doses of 800-1,600 mg of SAMe by mouth for up to 6 weeks.

Doses of SAMe have been given through IV or injected into the muscle, ranging from 200 to 400 mg daily at most 8 weeks.

Doses of 1,000-1,600 mg have been taken by mouth daily for 15 days to 6 weeks.

Doses of 150-400 mg given through IV daily for 3-4 weeks are most common.

A dose of 400 mg of s-adenosyl-L-methionine 1,4-butanedisulphonate stable salt (Knoll Farmaceutici S.p.A., Liscate, Milan, Italy) has been injected into the muscle daily.

Doses of 75-200 mg of SAMe have been injected into the muscle for 14-30 days.

Doses of 200-400 mg of SAMe per 250 milliliters of saline have been given through IV during the first three days of treatment, followed by 400 mg of SAMe daily on days 4-14.

Use the methylation index ELISA kit developed in this invention to measure methylation index once every 3-5 days for patients who take higher dosage (more than 400 mg daily) to adjust the dosages of SAMe timely. If the methylation index increases too fast (increase 5 folds between measures or by 0.5 or when patients can experience obvious symptoms associated with using SAMe), reduce dosage is recommended especially for patients who have high blood pressure or other cardiovascular problems. High risk groups should have methylation index tested daily or use the SAM and SAH rapid test kid to qualitatively or semi-quantitatively test SAM and SAH levels in blood or urine daily to ensure the safety of SAM administration to avoid any side effects.

For those who take SAM-e less than 400 mg daily by mouth, have methylation index tested, or at least SAM tested when needed, or just have it tested weekly to get some idea of whether the dosage is right for the patient as well as when to stop taking the medicine.

Do not stop SAM medication unless methylation index is back to normal and stabilized for a week or two.

For those depression patients who have normal or close to normal methylation index, do not use SAMe as the first choice of therapeutics. Instead, use other type anti-depression medicines. But methylation index may still be a good marker to monitor the effectiveness of other treatment. Have methylation index tested regularly is still important to determine when the treatment can be stopped.

Example 21

Measuring methylation index from urine (or blood sample if urine cannot be used normally because of some specially components in it or the concentration of SAM in urine is too low) is a good way to personalize liver and/or cholestasis therapeutics. SAM-e therapeutical protocol may look like this:

For adult patients, depending on the severity of the liver and/or cholestasis and other health problems, many regimens have been used, for example:

1,600 mg of SAMe has been taken by mouth daily for 2 weeks.

A dose of 1,000 mg has been injected into the vein (IV) daily for 4 weeks.

To treat bile flow problems in pregnancy, 500 mg of Transmetil® has been given by slow infusion twice daily for 14 days, followed by 500 mg of SAMe taken by mouth twice daily until or after delivery. A dose of 600 mg of Samyr® has been taken by mouth alone.

A dose of 1,800 mg of Samyr® has been taken by mouth together with beta-mimetics daily.

A dose of 500 mg has been taken by mouth twice daily.

Doses of SAMe that have been given include: 1,000 mg injected into the muscle daily until delivery, 200 or 800 mg given through IV daily for 20 days; 800 mg given through IV daily in two divided doses until delivery; 800 mg given through IV; and 800 mg given through IV over three hours for 20 days. A dose of 800 mg of disulfate-p-toluene sulfonate stable salt (BioResearch, S.p.A, Milan, Italy) has been given through IV daily.

Use the methylation index ELISA kit developed in this invention to measure methylation index once every 3 days for patients who take higher dosage (more than 600 mg daily) to adjust the dosages of SAMe timely. If the methylation index increases too fast (increase 5 folds between measures or by a certain number when patients can experience obvious symptoms associated with using SAMe), reduce dosage is recommended especially for patients who have high blood pressure or other cardiovascular problems. High risk groups should have methylation index tested daily or use the SAM and SAH rapid test kid to qualitatively or semi-quantitatively test SAM and SAH levels in blood or urine daily to ensure the safety of SAM administration to avoid any side effects.

For those who take SAM-e less than 600 mg daily by mouth, have methylation index tested, or at least SAM tested when needed, or just have it tested weekly to get some idea of whether the dosage is right for the patient as well as when to stop taking the medicine.

Do not stop SAM medication unless methylation index is back to normal and stabilized tier a week or two.

All patents, patent applications and publications cited in this application including all cited references in those patents, applications and publications, are hereby incorporated by reference in their entirety for all purposes to the same extent as if each individual patent, patent application or publication were so individually denoted.

While the many embodiments of the invention have been disclosed above and include presently preferred embodiments, many other embodiments and variations are possible within the scope of the present disclosure and in the appended claims that follow. Accordingly, the details of the preferred embodiments and examples provided are not to be construed as limiting. It is to be understood that the terms used herein are merely descriptive rather than limiting and that various changes, numerous equivalents may be made without departing from the spirit or scope of the claimed invention.

What is claimed is:

1. A method of providing a therapeutic drug treatment for mammal diseases of the liver selected from the group consisting of hepatitis, cholestasis, liver cirrhosis and fibrosis, the method comprising:
    (a) measuring the methylation index in body fluids from a subject having said liver diseases, said methylation index being measured by a method comprising: (i) obtaining a sample from body fluids; (ii) mixing said sample with a monoclonal antibody specific for S-adenosylmethionine, wherein said monoclonal antibody is derived from hybridomas having the designation from the China Center For Type Culture Collection (CCTCC) number C2017178 and number C2017179; (iii) detecting the binding of S-adenosylmethionine present in said sample with said antibody; (iv) quantifying the binding as a measure of the amount of S-adenosylmethionine present in said sample; (v) determining the concentration of S-adenosylhomocysteine using conventional immunoassay technology and (vi) calculating the ratio of S-adenosylmethionine/S-adenosylhomocysteine to provide the methylation index of said biological sample; and
    (b) administering effective amounts of S-adenosylmethionine or pharmaceutically acceptable salts thereof to provide a therapeutic treatment with a likelihood of being effective for said mammal subject having said liver diseases based on the methylation index levels in said body fluids and wherein said methylation index level is <4.

* * * * *